United States Patent [19]
Federowicz et al.

[11] Patent Number: 5,927,273
[45] Date of Patent: Jul. 27, 1999

[54] COMBINED LIQUID VENTILATION AND CARDIOPULMONARY RESUSCITATION METHOD

[75] Inventors: Michael G. Federowicz, Rancho Cucamonga, Calif.; Ronald M. Klatz, Chicago, Ill.

[73] Assignee: Life Resuscitation Technologies, Inc., Chicago, Ill.

[21] Appl. No.: 08/813,330

[22] Filed: Mar. 7, 1997

Related U.S. Application Data

[60] Provisional application No. 60/013,049, Mar. 8, 1996, and provisional application No. 60/037,335, Jan. 2, 1997.

[51] Int. Cl.$^6$ .......................... A62B 37/00; A61M 15/00; A61M 16/00
[52] U.S. Cl. ...................................... 128/200.24; 128/913
[58] Field of Search .......................... 128/204.18, 200.24, 128/913

[56] References Cited

U.S. PATENT DOCUMENTS

| | | |
|---|---|---|
| 3,232,292 | 2/1966 | Schaefer . |
| 3,971,385 | 7/1976 | Corbett . |
| 4,173,654 | 11/1979 | Scherer . |
| 4,232,665 | 11/1980 | Vaseen . |
| 4,424,806 | 1/1984 | Newman et al. . |
| 4,451,251 | 5/1984 | Osterholm . |
| 4,657,532 | 4/1987 | Osterholm . |
| 4,805,609 | 2/1989 | Roberts et al. . |
| 5,084,011 | 1/1992 | Grady . |
| 5,085,630 | 2/1992 | Osterholm . |
| 5,158,536 | 10/1992 | Sekins et al. . |
| 5,195,942 | 3/1993 | Weil et al. . |
| 5,200,176 | 4/1993 | Wong . |
| 5,238,683 | 8/1993 | Crystal . |
| 5,259,371 | 11/1993 | Tonrey . |
| 5,272,252 | 12/1993 | McLean . |
| 5,308,320 | 5/1994 | Safar et al. . |
| 5,335,650 | 8/1994 | Shaffer et al. . |
| 5,395,314 | 3/1995 | Klatz et al. . |
| 5,403,834 | 4/1995 | Malfroy-Camine . |
| 5,411,474 | 5/1995 | Ott et al. . |
| 5,413,558 | 5/1995 | Paradis . |
| 5,437,272 | 8/1995 | Fuhrman . |
| 5,655,521 | 8/1997 | Faithfull et al. . |

OTHER PUBLICATIONS

"Active Compression Decompression: A Novel CPR Technique", The Jounal of Invasive Cardiology, pp. 114–118, V5, No. 3, Apr. 1993, Bruce Goldner & Todd Cohen.

IEEE Transactions On Biomedical Engineering, vol. BME–22, No. 5, pp. 412–417, Sep. 1975, T.H. Shaffer et al., "An Electromechanical Demand Regulated Liquid Breathing System".

(List continued on next page.)

*Primary Examiner*—Kimberly L. Asher
*Attorney, Agent, or Firm*—Oliff & Berridge, PLC

[57] ABSTRACT

A method and apparatus utilize liquid ventilation to increase the efficacy of cardiopulmonary resuscitation (CPR). The method involves replacing gas in the lungs with an oxygen and carbon dioxide carrying liquid to eliminate the decreased pumping efficiency of the heart seen during conventional or active compression-decompression (ACD) closed-chest CPR. A further advantage during ACD-CPR is the ability to perform liquid ventilation without a mechanical respirator. A further advantage is provided by supplying a continuous flow of liquid (or gaseous) ventilation medium throughout the entire chest compression/re-expansion cycle, dramatically accelerating both gas exchange and cooling or warming of the patient or animal subject.

12 Claims, 7 Drawing Sheets

OTHER PUBLICATIONS

Program and Abstracts for the 26$_{th}$ Educational and Scientific Symposium, Official Journal of the Society of Critical Care Medicine, vol. 25/No. 1 (Suppl.), Jan. 1997.

"Attempts at Liquid Breathing, Technologies May Save Preemies, Treat Illnesses", by Tim Friend, USA today, May 31, 1994, p. 05D.

Cryo Care Report, Apr. 1996, No. 7, A Bypass on the Way to Bypass.

"Easier Breathing in RDS", Medical Tribune, Jan. 11, 1990.

"Partial Liquid Ventilation Promising in Preemies with Severe RDS," by Calvin Pierce, No. 1994.

"New Ventilation Technique Offers Better Patient Cooldown", Venturist Monthly News vol. 8(9) Sep. 1996, #93.

"Cardiac Output During Liquid (Perflourocarbon Breathing In Newborn Piglets", Scott E. Curtis, MD et al., Official Journal of the Society of Critical Care Medicine, vol. 19, No. 2, Feb. 1991, pp. 225–230.

"The Effects of Liquid Ventilation of Cardiopulmonary Function in Preterm Lambs", by Thomas H. Shaffer et al., Pediatric Research—An International Journal of Clinical Laboratory and Developmental Investigation, vol. 17, No. 4, Apr. 1983, pp. 303–306.

"Instrumentation for Measuring Cardiac Output by Direct Fick Method During Liquid Ventilation", by E.M. Sivieri et al., Undersea Biomedical Research, vol. 8, No. 2, Jun. 1981, pp. 75–83.

"Decompression Incidence In Air—And Liquid Breathing Hamsters", by P.R. Lynch et al. Undersea Biomedical Research, vol. 10, No. 1, Mar. 1983, pp. 1–10.

"Liquid Ventilation in Dogs: An Apparatus for Normobaric and Hyperbaric Studies", by D.J. Harris et al., Journal of Applied Physiology, vol. 54, No. 4, ISSN 0161–7567, Apr. 1983, pp. 1141–1148.

COMBINED LIQUID VENTILATION AND CARDIOPULMONARY RESUSCITATION METHOD

This nonprovisional application claims the benefit of U.S. Provisional Application No. 60/013,049, filed Mar. 8, 1996 and U.S. Provisional Application No. 60/037,335, filed Jan. 2, 1997.

FIELD OF THE INVENTION

The invention relates to an apparatus and method for treating patients suffering from trauma such as cardiac arrest. More particularly, the present invention relates to an apparatus and method utilizing liquid ventilation to increase the efficacy of resuscitation techniques, i.e., cardiopulmonary resuscitation (CPR). The method involves replacing gas in the lungs with an oxygen carrying liquid. The method can act to greatly increase the effectiveness of conventional resuscitation techniques. The invention also relates to a method and apparatus for continuously providing liquid ventilation fluid, i.e., breathing liquid, to a patient. The methods can be used to rapidly cool and/or rewarm the patient.

BACKGROUND OF THE INVENTION

During cardiac arrest, the heart does not pump blood, and thus the brain does not receive freshly oxygenated blood. Irreversible neurological damage begins soon after circulation stops. Thus, it is imperative that oxygenated blood be continuously supplied to the brain and other vital organs by artificial means during cardiac arrest to insure that the patient will survive neurologically intact and without significant brain damage after resumption of cardiac function.

Conventional resuscitation techniques such as CPR, heart massage and electroshock treatments are notoriously inefficient in maintaining the supply of oxygenated blood within the body. Among cardiac arrest victims overall, less than 10% survive neurologically intact and without significant brain damage. Presently, the majority of patients die or sustain some neurological injury from ischemia (lack of blood flow to the brain) or anoxia (lack of oxygen to the brain). Additional disadvantages of the conventional techniques are discussed in the U.S. Pat. No. 4,424,806, the entire contents of which is incorporated herein by reference.

The reason the conventional techniques of resuscitation have such a high rate of morbidity and mortality are numerous, but are believed to be focused upon the following factors. Conventional resuscitation techniques typically supply only 25 to 30% of resting cardiac output and provide a mean arterial pressure (MAP) of only 30 to 45 mm Hg, compared to the 50 to 55 mm Hg MAP minimally required to maintain brain viability for even short periods of time.

A first factor in the inefficiency is that the lungs, which are normally gas-filled, form compliant compartments. As such, during CPR, the compartments act to dampen or decrease the effectiveness of the force applied as a compression to the chest. Thus, the intrathoracic pressure, i.e., the "thoracic pump," and not the force applied to the chest, determines the amount of cardiac output during CPR. The lungs act to decrease the intrathoracic pressure.

As a further factor, during normal heart operation, blood rich in oxygen and poor in carbon dioxide returns from the lungs to the left atrium and enters the left ventricle, which contracts and forces the blood into the aorta for distribution throughout the body. The flow is maintained by the mitral valve, which regulates the flow by opening and closing during contractions of the left ventricle. However, during conventional resuscitation techniques, the compression and decompression does not fully close the mitral valve. This results in regurgitation of the blood in the left ventricle into the heart and consequently, low cardiac output.

As a third factor, during CPR, the thoracic vena cava and the right atrium are compressed, resulting in an abnormally high venous pressure. This is related to a corresponding decrease in the volume of deoxygenated blood returning to the right heart. This results in an inadequate preload, i.e., inadequate volume of oxygen depleted blood in the heart, and thus a further reduction of the resultant cardiac output.

Finally, pulmonary edema, which results from a high pulmonary artery pressure and central venous pressure develops rapidly during conventional resuscitation techniques. This compromises gas exchange with the blood in the lungs and thus further reduces the efficiency of conventional resuscitation techniques.

It is in many instances also desirable to chill and/or warm patients during treatment. For example, patients suffering from sudden cardiac arrest, shock, severe hypotension, or ischemia may need rapid reduction in body temperature in order to reduce metabolic demands to levels capable of being provided for by compromised body systems or conventional resuscitation techniques, or otherwise to provide specific protection afforded to organs by rapidly inducing and maintaining hypothermia after an ischemic or traumatic event. Similarly, it is desirable to rewarm patients, for example, patients who no longer need a reduced body temperature or who have otherwise experienced accidental hypothermia.

Chilling and/or rewarming of patients is traditionally done externally to the body, for example by applying ice packs or with refrigeration. These methods produce very slow cooling. Newer methods involving cold intracarotid infusion or intraperitoneal infusion, etc. are faster, but would also be more effective still when combined with other cooling modalities. A simpler and less invasive cooling method that is consistent with current practices would be very beneficial.

U.S. Pat. No. 5,158,536 to Sekins discloses a method for treating lung cancer in which warm fluid is introduced into the lungs and then removed from the lungs in rhythmic patterns.

SUMMARY OF THE INVENTION

It is an object of this invention to provide an easily employed method for increasing the efficiency of CPR. It is another object of the invention to attain unprecedented rates of whole body cooling by non-invasive and mechanically simple means.

It is another object of this invention to provide an apparatus that is easily deployed and preferably transportable for use in the method. It is a still further object of the invention to develop an apparatus that can effectively continuously supply and withdraw a breathing liquid from the lungs of a patient.

These and other objects are achieved in the present invention by the use of liquid ventilation, and most preferably continuous flow (or sweep flow) liquid ventilation in combination with CPR. The liquid ventilation can act as an efficient aid to compression and decompression on the heart and can act as a constant supply of oxygenated fluid for blood during compression and decompression of the heart through CPR. The liquid ventilation can also act to readily achieve rapid rates of whole body cooling. The present method shows that the above-discussed method of Sekins and similar methods are decidedly sub-optimal.

The present invention also includes an apparatus for evacuating the lungs of air and other material, for delivering an oxygen rich liquid to the lungs, and for removing oxygen depleted and carbon dioxide containing fluid from the lungs. The flow is preferably continuous, but may also be pulse flow.

BRIEF DESCRIPTION OF THE DRAWINGS

The invention will be described in more detail with reference to the attached drawings, wherein.

DETAILED DESCRIPTION OF PREFERRED EMBODIMENTS

Figure 1:
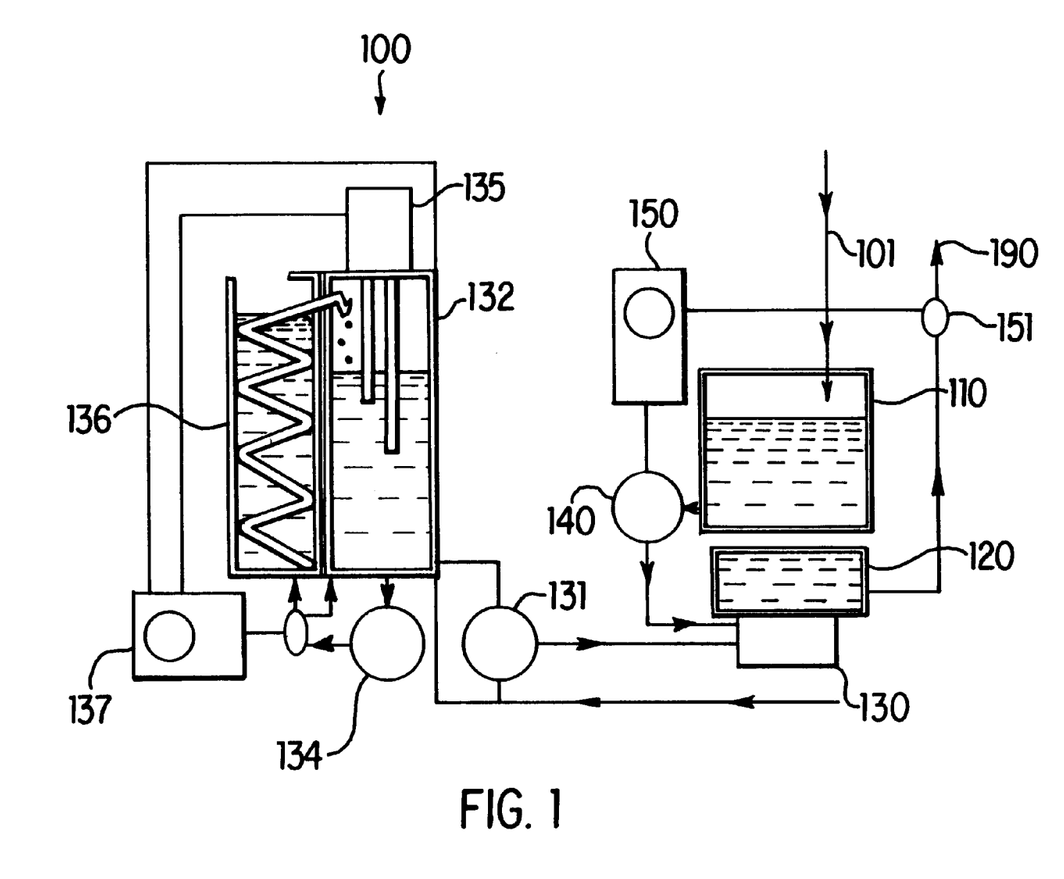
FIG. 1 is a front view of an apparatus used in one embodiment of the invention.

An apparatus for carrying out the liquid ventilation in one embodiment of the present invention, which is preferably a continuous liquid flow ventilation, is illustrated in FIG. 1. In the apparatus 100, breathing liquid returns from a patient via tube 101, and is pumped to the patient through tube 190. These tubes 101 and 190 connect to a tracheal tube placed into the patient as discussed more fully below.

A breaching liquid is stored in a reservoir 110, into which oxygen depleted breathing liquid from the patient flows. The oxygen depleted breathing liquid is preferably filtered or otherwise treated prior to being deposited into the reservoir in order to remove waste and/or contaminants from the oxygen depleted liquid.

Flow of the breathing liquid is controlled by pump 140. The pump 140 is preferably a centrifugal pump. The pump is attached to a pressure controller 150, which is connected to a pressure control valve in tube 190 leading to the patient. The valve and controller measure the pressure of liquid within the patient, and thus are used to control the proper continuous flow rate of breathing liquid into the patient. If an unacceptably high pressure in the lungs is detected by the controller, the valve shuts off the flow of liquid into the patient.

Prior to entering tube 190, the breathing liquid from the reservoir 110 is directed by the pump through an oxygenator 120 and heat exchanger 130. The oxygenator 120 may be any suitable device for adding oxygen to the breathing liquid, as discussed more fully below. The oxygen is preferably supplied from oxygen tanks. The heat exchanger 130 may be used to either cool or heat the breathing liquid, as desired. The heat exchanger contains an appropriate liquid or gas which can be cooled or heated.

Flow of the heat exchange medium is controlled by pump 131, which carries liquid to the heat exchanger 130. The medium is stored in reservoir 132, where it can be heated, for example by heating element 135, or cooled, for example in region 136. A heat exchange medium recirculating pump 134 and temperature controller 137 ensure that the medium is at the desired temperature.

Once oxygenated and at the proper temperature, the breathing liquid is fed into tube 190 for delivery into the lungs of a patient who has been intubated.

While the apparatus 100 is shown as a large device, it is possible to provide the device in transportable form, for example as discussed in the embodiments below. Further, although the device has been described as providing continuous flow of breathing liquid, the device may also be used with pulse flow, wherein breathing liquid is supplied and withdrawn in intervals mimicking actual breathing. For example, the lungs may be filled with the breathing liquid, maintained in the lungs during CPR, and then removed from the lungs. The lungs may thereafter be re-filled with oxygenated breathing liquid or gas and CPR continued. The pulse flow and CPR may be continued as necessary until a normal heart rhythm is developed. The pulse and removal of breathing liquid preferably occurs between 3 and 7 times per minute, depending on the patient.

Although the filling and emptying of the lungs with breathing liquid during the pulses correspondingly compresses and decompresses the heart to assist in CPR, pulse flow supply of breathing liquid in conjunction with external CPR has a drawback in that the application of external thoracic pressure may be suspended during emptying and re-filling of the lungs. Continuous or sweet flow supply and withdrawal of breaching liquid is thus preferred in that external CPR need not be suspended and ventilation is continuously supplied by the breathing liquid.

Figure 2A:
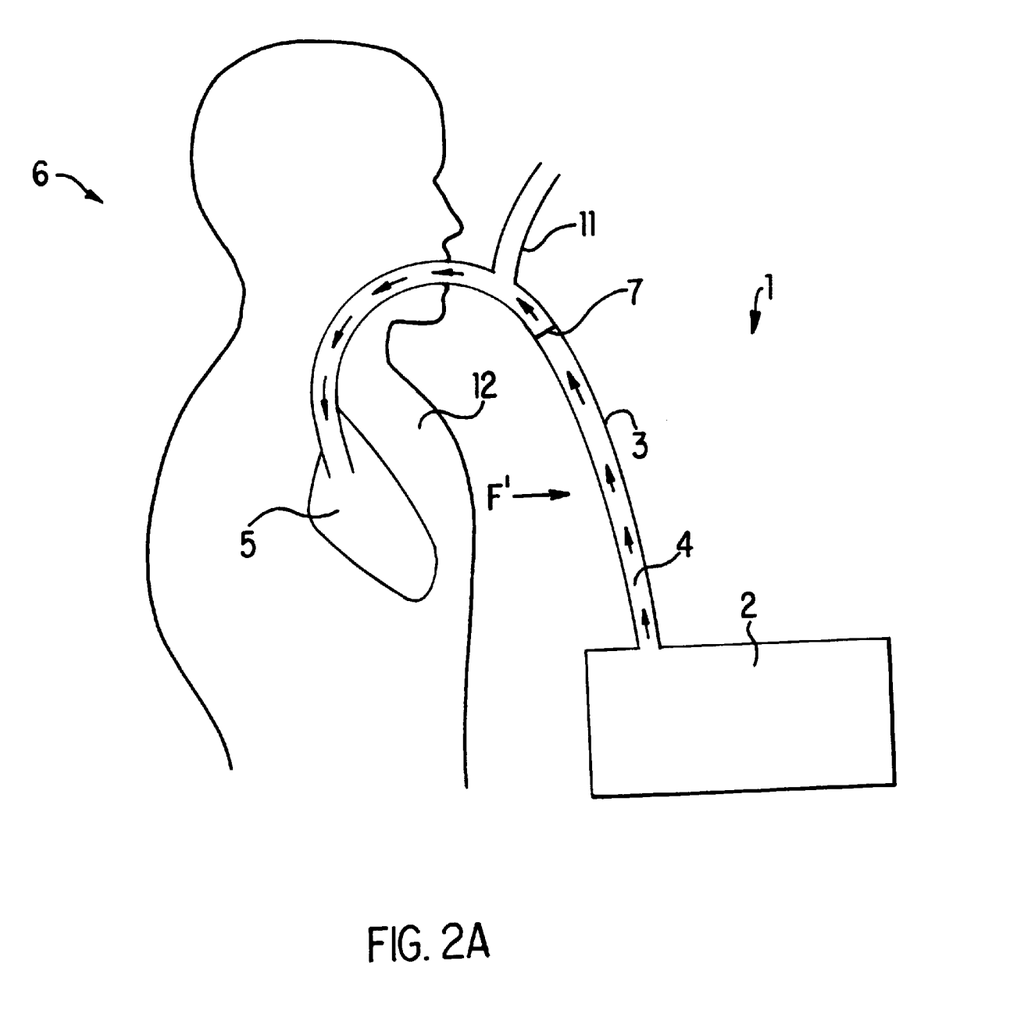
FIG. 2A shows the liquid flow into the lungs during the method, for example during a compression-releasing phase of the CPR cycle, in one embodiment of the invention.
Figure 2B:
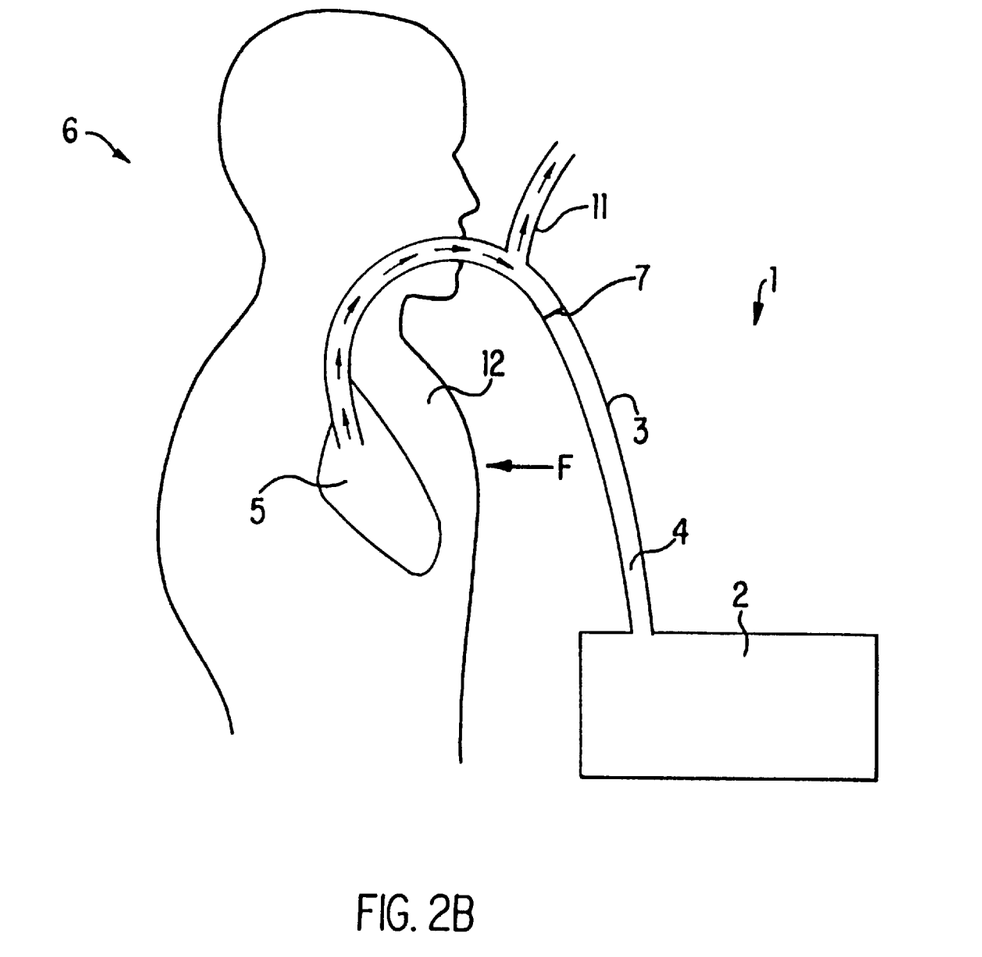
FIG. 2B shows the liquid flow from the lungs in the method, for example during the compression-phase of CPR, in the embodiment of the invention shown in FIG. 2A.

Referring to FIGS. 2A and 2B, the method of the invention is illustrated in a simple manner to illustrate the flow of an oxygenated liquid into and out of the lungs of a patient. Liquid ventilation is provided in conjunction with CPR so as to increase the efficacy of CPR.

The apparatus 1 in the embodiment of FIGS. 2A and 2B includes a liquid reservoir 2, a tubular member 3 connected to the reservoir 2 for receiving and transporting liquid 4 to lungs 5 of a mammalian body 6, a one-way valve member 7 within the tabular member 3, wherein the valve member 7 is capable of permitting a first predetermined volume of liquid 4 to enter the lungs 5 during the compression-releasing phase (when the net force (F') acting on the thoracic cavity 12 of the mammalian body 6 is negative) (FIG. 2A). The valve member 7 is capable of preventing a volume of liquid 4 from exiting the lungs 5 during the CPR compression phase (when an external pressure F is applied to the thoracic cavity 12) (FIG. 2B)). Also provided is a shunt member 11 connected to the tubular member 3 and located between the valve member 7 and the lungs 5. The shunt member 11 can act in conjunction with the valve 7 to divert liquid 4 away from the lungs 5 when a net positive force is applied to the thoracic cavity 12.

The liquid 4 shunted from the lungs may be reoxygenated by an oxygenator (not shown) and subsequently reintroduced into the lungs 5. The oxygenator may comprise a membrane oxygenator through which breathing liquid to be oxygenated is passed. Such a process for oxygenating blood is disclosed in U.S. Pat. No. 5,308,320, the entire contents of which is incorporated herein by reference.

In this method, the free end of the tubular member 3 (not shown) is inserted into the trachea of the patient, preferably at a position just above the point where the trachea divides into the two main-stem bronchi (the carina). The lungs are preferably evacuated of gas and other materials prior to introduction of the oxygen rich liquid, for example by compressing the patient's chest or with a vacuum device that may or may not be associated with the liquid ventilation apparatus. The oxygen rich liquid 4 is then introduced into the lungs 5 from the liquid reservoir 2 through the tubular member 3. Introduction of the liquid 4 may be achieved through the pulling of the liquid 4 into the lungs 5 during the compression-releasing phases of CPR.

However, introduction of the liquid 4 into the lungs 5 is preferably achieved by pumping or draining by gravity the liquid 4 from the liquid reservoir 2 into the tubular member 3. The apparatus thus may also include a pump (not shown) to move the liquid 4 from the liquid reservoir 2 to the tubular member 3. The pump may be manually powered. An example of a manually powered pump can be found in U.S. Pat. Nos. 5,413,558 and 5,195,942, the entire contents of which are incorporated herein by reference. The pump may also be powered by an AC or DC power source, such as a battery gel-pak. Examples of such devices can be found in U.S. Pat. No. 5,308,320.

In a preferred embodiment of the invention, the valve 7 is not a completely one-way valve, but rather permits liquid to pass in both directions. This allows for continuos flow of breathing liquid to and from the lungs. The flow of liquid 4 toward the lungs 5 encounters less resistance from the valve 7 than does the flow away from the lungs. The difference in resistance may be selected to permit the valve 7 to act as a safety valve which maintains a substantially constant amount of liquid 4 in the lungs 5, but permits the liquid 4 to escape the lungs 5 when the pressure in the lungs 5 approaches a harmfully high level.

Thus, according to the invention, continuous ventilation may be carried out instead of the conventional procedure of pausing and interrupting chest compressions to interpose a ventilation. By placing a fenestrated, wire-reinforced, thin wall tube down the tracheal tube at the level of the carina (the two main bronchi), or slightly above, a continuous stream of oxygenated and low carbon dioxide-containing liquid breathing medium can be delivered to the large airways. Transport of this oxygenated and low carbon dioxide-containing breathing liquid can then be distributed to the lungs by the use of Active Compression/ Decompression CPR (ACD-CPR), wherein each downstroke is followed by an upstroke using a suction cup device, such as the Ambu Cardiopump (Ambu International), with approximately 18 kg of negative pressure. The cycle of external thoracic compression followed by thoracic decompression at a rate of 60 to 100 compressions/decompressions per minute allows for an exchange of liquid between the constantly replenished sump of oxygenated and carbon dioxide-cleansed liquid in the large airways, and the oxygen depleted and carbon dioxide-laden liquid in the alveoli of the lungs.

Figure 3:
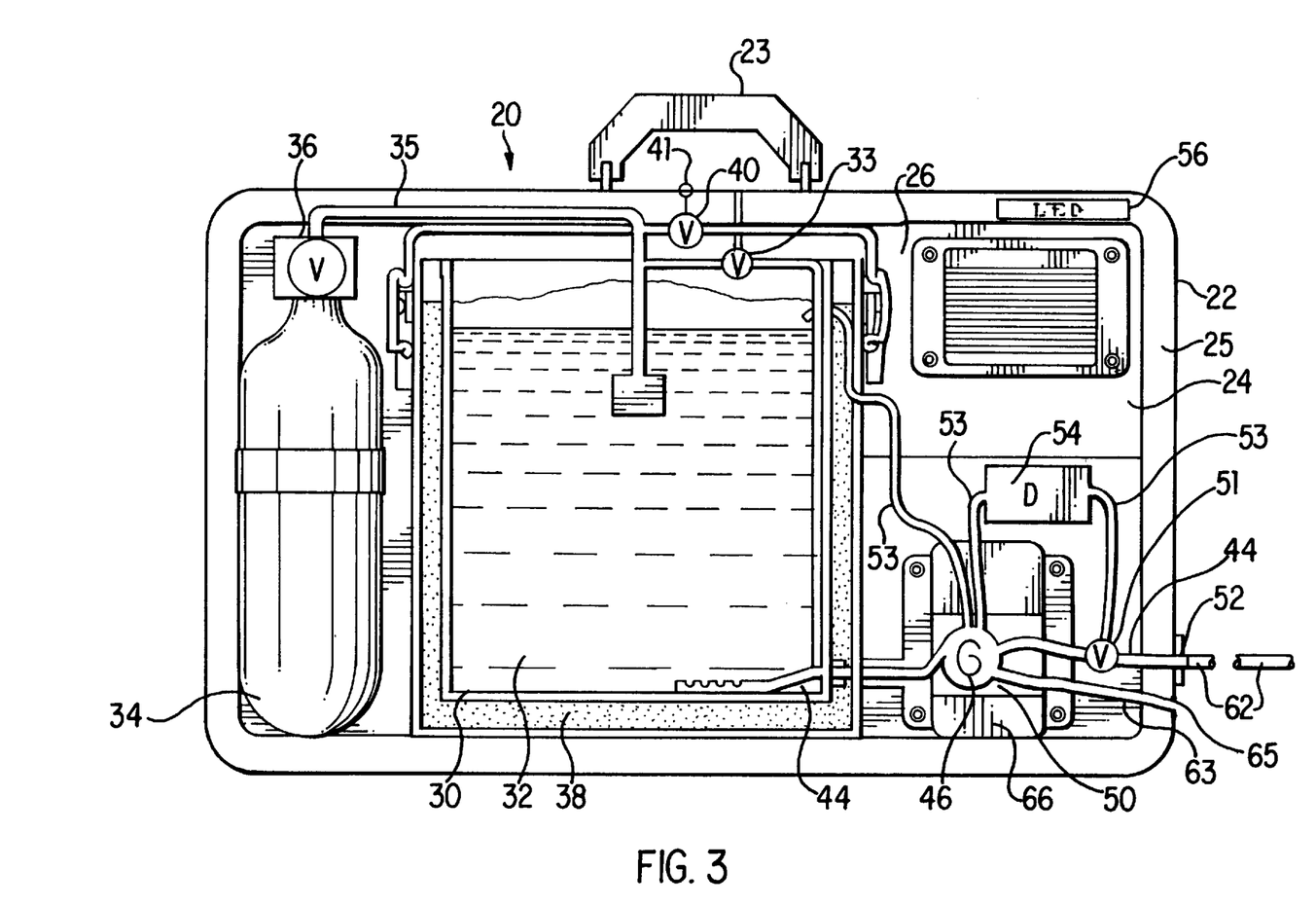
FIG. 3 is a front view of another apparatus used in another embodiment of the invention.
Figure 4:
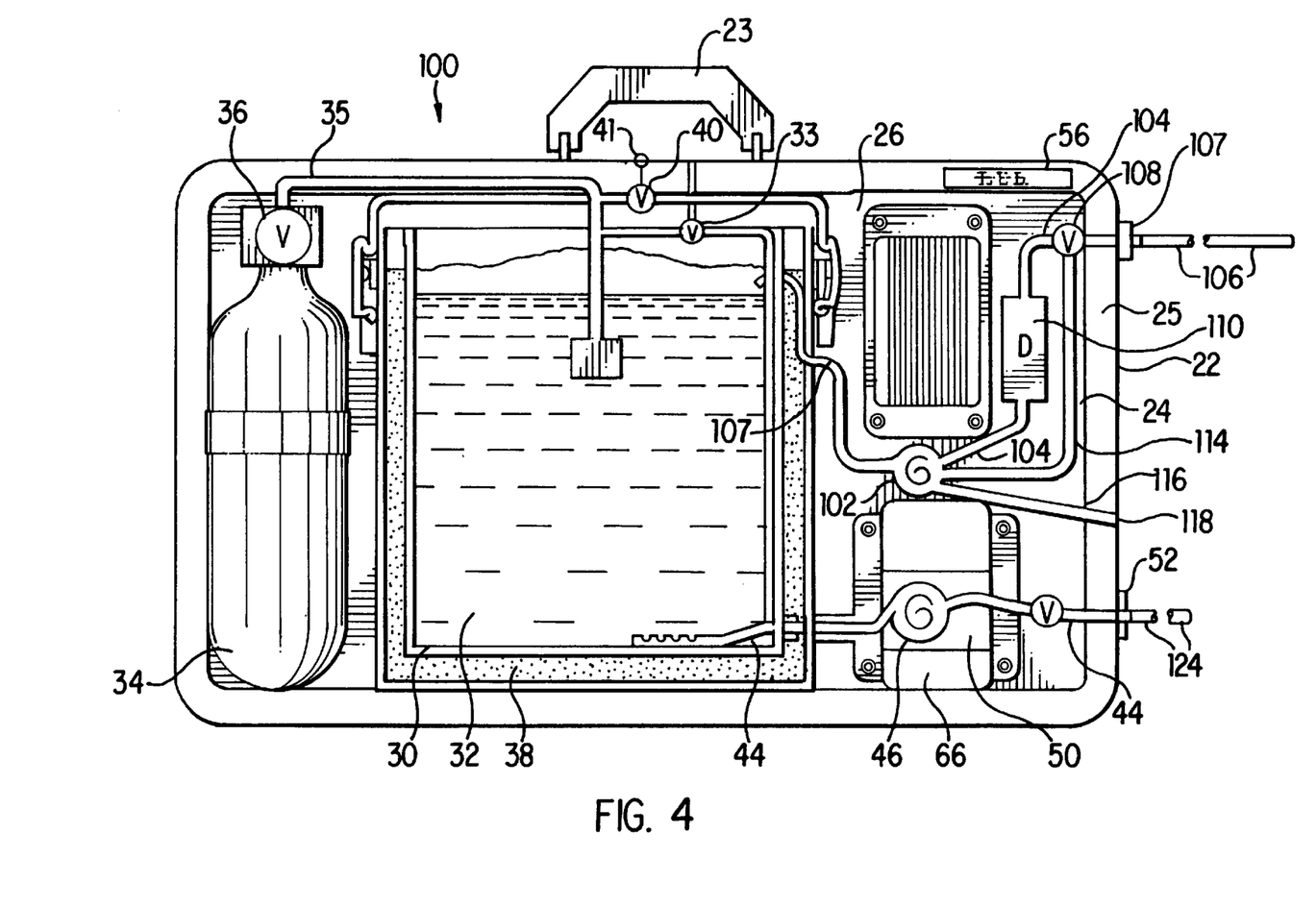
FIG. 4 is a front view of another apparatus used in another embodiment of the invention.

Devices for carrying out the liquid ventilation in another embodiment of the invention are illustrated in FIGS. 3 and 4. Both devices 20, 100 of FIGS. 3 and 4 are illustrated as being relatively small. They are portable, suitcase-like in appearance, and suitable for field use, such as in ambulances, battlefields, athletic fields, aircraft, marine vehicles, spacecraft, emergency treatment facilities, and the like. They are lightweight and can be carried directly to the patient. In one example of the device, the outer casing measures forty inches by twenty four inches by twenty inches and weighs approximately fifty pounds. They are also suited for stationary, clinical use. Should a clinical device be desired, the devices could be made larger and modified accordingly for such use, for example as illustrated in FIG. 1.

Referring to FIG. 3, the preferred device 20 of the invention may be automatic or semi-automatic. The device 20 includes an outer casing 22 with a handle 23 and a window 24. The window 24 is located within a first side 25 which has a greater width than length. The casing 22 includes an inner chamber 26. This inner chamber 26 contains components which include a reservoir 30, an oxygen tank 34, a heat exchanger 38, a pump 46, a logic control unit 50, and a power source 54.

The reservoir 30 holds the oxygen-containing liquid or solution. The liquid breathing solution of this invention may be a fluid mixture of various components. Fluids known in the art to be consistent with use in this application include Perflubron™ and a variety of fluorocarbon compounds, including FC11, etc. Other suitable breathing liquids are discussed in U.S. Pat. No. 5,158,536, which is incorporated herein by reference.

The liquid ventilation fluid is preferably packaged in premixed, premeasured canisters, for a single immediate use. These canisters can be replenished (refilled) and exchanged for continued application. Preferably, this reservoir 30 is adapted to hold up to ten liters of fluid contained within replaceable canisters 32. The preferred canisters are clear plastic bags, such that fluid depletion in the reservoir 30 can be viewed through the window 24. However, these canisters can be rigid containers, made of opaque materials, such as plastic, metal or the like. These canisters 32 may be equipped with pressure relief valves 33.

An oxygen tank 34, adjustable to various pressures, communicates with reservoir 30 through a first conduit 35. Oxygen tank 34 is sealed by a valve 36, which is opened once the device 20 is activated. Tank 34 contains oxygen pressurized to at least above atmospheric pressure. Tank 34 could also hold gases such as carbon dioxide, hydrogen or nitric oxide, and trace therapeutic gases.

A heat exchanger 38, capable of controlling the breathing liquid's temperature, surrounds reservoir 30. Preferably the heat exchanger cools by undergoing an internal endothermic reaction, once a charging valve 40 is opened when a charging handle 41 on the device is activated. The exchanger may contain, for example, ammonium nitrate and water, which are initially separate. Upon activation, these chemicals contact each other, reacting endothermically, causing the heat exchanger to cool. Additionally, the heat exchanger's cooling can be accomplished by carbon dioxide (dry ice), freon (or other refrigerant gases) or liquid $CO_2$ or other compressed gases, or a mechanical cooling device. The initial liquid ventilation liquid temperature may be as low as $-6°$ C., since it will gain heat upon entering the body and therefore has been found not to cause freezing damage to the lungs despite very rapid induced body cooling.

Alternately, the heat exchanger 38 may contain chemicals that create an exothermic reaction for increasing the breathing liquid temperature above body temperature (as high as 125° F.) and/or an electric heating element (powered by the logic control unit 50 and the energy source 66), or other mechanical heating element.

A second conduit 44 extends from the reservoir and communicates with a valve controlled pump 46, capable of pumping at various rates, directions (forward and reverse) and modes, in communication with a logic control unit 50. A filter (not shown) could be placed alone the second conduit to remove unwanted contaminants.

The second conduit 44 extends through the pump 46 and logic control unit 50 through a two-way valve 51 and terminates in a side opening 52 on the device 20. This two-way valve 51 also controls flow of solution through a third conduit 53 for treatment in a defoaming and filtration unit 54 (hereinafter "defoaming unit") prior to reentry into the reservoir 30. Preferably, this side opening 52 is on the side 60 adjacent to the longitudinal side 25. Side opening 52 is capable of attaching to a tube 62, that connects to an endotracheal tube in a patient (the patient having been intubated) at an adapter, such that liquid can enter the patient's airway and ultimately the lungs, in accordance with the method of the invention.

The third conduit 53 extends from the two-way valve 51 to the valve controlled pump 46 and extends to the reservoir 30. The defoaming unit 54 is preferably along the third conduit 53, intermediate between the two-way valve 51 and the valve controlled pump 46. Alternately, the defoaming unit 54 could be placed along the third conduit 53 intermediate between the valve controlled pump 46 and the reservoir 30. The valve controlled pump 46 draws the liquid that was treated in the defoaming unit 54, and pumps it into the reservoir 30, through the third conduit 53. The defoaming unit 54 includes a defoamer, a carbon dioxide scrubber and a filter(s). Suitable defoaming units include those commercially available models such as the ULTIPOR® blood filter EC3840 from Pall Biomedical Products Corporation, East Hills, N.Y. 11548, in combinations of one or more.

This valve controlled pump 46 may also control flow to a waste conduit 63 that allows waste (fluids, gases, solids, including used liquid, bodily fluids or secretions and tissue particulates, or other material) to leave the device 20. Specifically, the waste exits the device through a side or top waste opening 65. Generally, such waste will float on a dense perfluorocarbon ventilation medium (density near 2).

The valve controlled pump 46 and the logic control unit 50 and two way valve 51 are powered by an energy source 66. However, the device is suitable for an electric adapter. A battery pack is the preferred energy source 66.

The logic control unit 50 preferably includes (not shown) an oxygen pressure sensor, a fluid mass flow sensor, a fluid volume indicator and regulator, a fluid pressure indicator and regulator, a fluid temperature indicator and regulator, a fluid temperature indicator with feedback to a mass sensor, and a timing device for estimating the time the fluid in the reservoir will be depleted at a given mass flow. The logic control unit 50 includes a microprocessor for controlling the movements of the valve controlled pump 46 and the two-way valve 51. However, the logic control unit 50 may be manually overridden as the valve controlled pump 46 and two-way valve 51 may be controlled manually. Measurements from the logic control unit 50 may be displayed on an LED or LCD digital display 56. Digital display 56 preferably shows the temperature and flow rate of the solution.

With respect to tube 62, high pressure respirator tubes, such as those typically used in high pressure respirators or ventilators or conventional heart-lung bypass pumps, are preferred. Additionally, it is preferred that the adjacent side 60 also contain openings for waste 65, for venting excess oxygen 68 and for oxygen intake 69. This oxygen intake can be from the atmosphere or from adjunct oxygen sources.

The device 2 is typically used in pulse flow applications. The device 20 is able to withdraw breathing liquid and waste from the patient by running the valve controlled pump 46 in reverse. When waste material is being removed, the two-way valve 51 opens the second conduit 44, such that liquid flows directly to the valve controlled pump 46, where it pumps in the forward direction to move the waste material out of the device 20 through the waste conduit 63. When spent breathing liquid is returned to the device 20 for treatment, the two-way valve 51 closes the second conduit 44 and opens the third conduit 53, such that spent breathing liquid is treated in the defoaming unit 54, returned to the valve controlled pump 46, and pumped to the reservoir 30, through the third conduit 53.

Liquid is infused into the lungs as the two-way valve 51 opens the second conduit 44, and closes the third conduit 53 (the valve controlled pump 46 is such that the third conduit 53 as well as the waste conduit 63 are closed). The oxygen tank valve 36 is opened and pressurized oxygen is released from the oxygen tank 34 into contact with the liquid breathing solution, thereby oxygenating it. The heat exchanger 38 is activated by releasing the charging valves 40. Once activated, the oxygenated solution in the reservoir 30 is cooled. This cooled solution moves through a second conduit 44, forced by sufficient pressure from the oxygen tanks 34 or drawn by sufficient pressure from the valve controlled pump 46 into the logic control unit 50. The pump 46 within this logic control unit 50 further moves the chilled oxygenated solution through this second conduit 44. Liquid then enters a tube 62, attached to an opening 52 in device 20 whereby it is delivered to the endotracheal tube (as placed in a previously intubated or tracheotomized patient) and ultimately to the lungs.

FIG. 4 shows another alternative device 100 of the invention. The device 100 is similar to the first device 20 disclosed above except that this device 100 includes two pumps. The first valve controlled pump 46 is similar to that disclosed for the first device 20 above, and the second valve controlled pump 102 receives solution from a third conduit 104, that is fed liquid through an inflow tube 106 (inflow of solution to the device 100) extending from the endotracheal tube of the patient. The second valve controlled pump 102 is controlled by the logic control unit 50 and includes a separate series of inflow and outflow conduits. The device 100 is preferably used in continuously supplying, while simultaneously withdrawing, breaching liquid to and from the lungs of a patient.

This third conduit 104 originates at a side opening 107. (The first and second conduits 35, 44 are similar to that disclosed for the device 20 above). A two-way valve 108, controlled by the logic control unit 50 (similar to that disclosed for the device 20 above), regulates liquid flow to the third conduit 104. A defoaming unit 110 is positioned along this third conduit 104 prior to its entering the second valve controlled pump 102. The defoaming unit 110 may be any of those disclosed for use in the first device 20. This third conduit 104 then exits the second valve controlled pump 102 and extends to the reservoir 30. The defoaming unit 110 may alternately be placed along this third conduit 104, between the second valve controlled pump 102 and the reservoir 30, if desired.

A fourth conduit 114 extends from the two-way valve 108 to the second valve controlled pump 102. This fourth conduit 114 is designed to carry waste, and liquid (if necessary) to the second valve controlled pump 102, where it is pumped through the waste conduit 116 and out of the device 100 through the side waste opening 118.

This device 100 forms a circular path for the breathing liquid, when it is used to perform the method of the invention. The logic control unit 50 is such that its microprocessor controls and coordinates the movements of the first and second valve controlled pumps 46, 102, (pumps and valves therein) and the two-way valve 108 to move liquid into and out of the device 100 (and into and out of the patient 72) along a circular path. The positioning of the two-way valve 108 and second valve controlled pump 102 to move material or liquid to the waste conduit 116 and out of the device when necessary, is also coordinated by the logic control unit 50. In this device 100, the side opening 107 receives the inflow tube 106. The side opening 107 communicates with the third conduit 104 that carries the liquid through the two-way valve 108, opened to the flow path of the third conduit 104, such that the spent breathing liquid is treated in the defoaming unit 110, moved to the second valve controlled pump 102 and returned (by pumping) back to the reservoir 30.

Liquid is infused into the lungs in a similar or identical manner as described above for the first device 20. The solution reaches the patient through an outflow tube 124 (outflow of liquid from the device 100), that connects with the device 100 at the side opening 52, and that merges with the inflow tube 106 at a Y-shaped end, joining the endotracheal tube at an adapter. A valve may be placed at the Y-shaped end for the purpose of increased control of directional flow of the solution such that there is minimal mixing of fresh (oxygenated) solution and spent solution in the inflow and outflow tubes 106, 124, and there is a minimization of dead space, such that the patient will inhale a minimal amount of spent solution. The valve is preferably a pressure controlled valve, responsive to pressure created by the directional flow of the solution. Alternately, the valve may be a mechanical, manually controlled or automatically controlled valve, subject to the control of the microprocessor in the logic control unit 50 (as connected by wires to the logic control unit 50). The only structural difference is that the second conduit 44 in this second device 100 lacks the two-way valve 51 (FIG. 3).

An alternative embodiment may have two or more reservoirs. These additional reservoir(s) can be formed by dividing the reservoir into multiple reservoirs or additional reservoirs can be connected to the reservoir of the device with an adapter mechanism.

Still additional alternative embodiments may use preoxygenated solution in the reservoirs. Reservoirs containing preoxygenated fluid solution eliminate the need for oxygen tanks as these devices have sufficient power (enhanced electronics and powerful pumps), capable of moving the solution from the reservoir in the device to the lungs.

An initial step of liquid ventilation involves instrumenting the trachea of the patient. This may be done by standard trachea intubation methods, preferably achieved with an endotracheal tube or other equivalent conduit. Alternately, an emergency tracheotomy (tracheostomy) may be performed in the neck in order to reach the trachea.

Once the trachea has been intubated or otherwise instrumented (such as by a tracheotomy), the tube for supplying and withdrawing breathing liquid is connected to the endotracheal tube by attachment with an adapter or the like.

Then, in the apparatus of FIG. 3, the valve controlled pump 46 is preferably activated in reverse, such that the device automatically draws a vacuum to evacuate the desired amount of air (for example, as much as 4 to 8 liters, or substantially the entire capacity of the lungs of an adult human) from the lungs. The material removed from the lungs during this evacuation step is brought into the device 20, with the valve in the pump 46 positioned such that this material enters the waste conduit 63 and leaves the device through the side waste opening 65. In FIG. 4, the second valve controlled pump 102 is initially activated with the two-way valve 108 opening the fourth conduit 114, to evacuate the lungs. Once sufficient pressure is drawn, the two-way valve 108 is closed as waste material is moved (by pumping) to the waste conduit 116, and leaves the device 100 through side opening 120.

Once the lungs are evacuated, in the device 20 (FIG. 3), the valve controlled pump 46 is switched to the forward direction. In the device 100 (FIG. 4), the first valve controlled pump 46 is now activated. In both devices 20, 100, the oxygen tank valve 36 is opened and pressurized oxygen is released from the oxygen tank 34 into contact with the liquid breathing solution, thereby oxygenating it. The heat exchanger 38 is activated by releasing the charging valve 40. Once activated, the oxygenated breathing liquid in the reservoirs is cooled. This cooled breathing liquid moves through a second conduit 44, forced by sufficient pressure from the oxygen tank 34 or drawn by sufficient pressure from the valve controlled pump 46 (first valve controlled pump 46 in the second device) into the logic control unit 50. The valve controlled pump 46 (first valve controlled pump 46 in the second device), within this logical control unit 50 further moves the chilled oxygenated solution through this second conduit. Liquid then enters the respective tube 62, (outflow tube) 124 attached to the side openings 52 in the devices 20, 100 whereby it is delivered to the endotracheal tube and ultimately to the lung.

The liquid is infused (pumped) to the lungs until it has replaced a desired amount or even substantially all of the air space and/or residual volumes of gas therein, ultimately filling the lungs, such that they are expanded. This typically requires 4 to 8 liters of breathing liquid. This expansion may compress the heart and great vessels (aorta, aortic arch, vena cava, pulmonary artery, pulmonary vein, subclavian artery, subclavian vein) within the thoracic cavity, located between the lungs. Additionally, this expansion creates increased intrathoracic pressure (positive pressure).

In the liquid ventilation resuscitation method, the liquid itself may expand the lungs with sufficient force to compress the heart and great vessels, resulting in cardiac outflow sufficient to provide a certain amount of circulation to the body. Some or most of the liquid may then be evacuated from the lungs by suction created by the pumps (for example, the second valve controlled pump 102 in the device 100). Evacuating the lungs deflates them, reducing their volume, thereby decreasing pressure on the heart and great vessels. Additionally, this decrease in pressure creates decreased intrathoracic pressure (negative pressure) which allows the heart and great vessels to expand, resulting in the blood being drawn back toward the heart, creating venous blood flow. In this method, the breathing liquid is supplied and withdrawn cyclically in a manner similar to normal breathing, typically between 3 and 7 times per minute. The efficiency is preferably increased by the application of external CPR, for example ACD-CPR.

These solution infusion and evacuation steps form a cycle that can be repeated as desired. This cycle is usually continued for as long as necessary to create circulation.

For example, the solution may be delivered in a series of pulses (pulsatile delivery). During pulsatile delivery, the valve controlled pumps on the devices are controlled to pump in both the forward and reverse directions. By pumping in both directions, the lungs may be evacuated and infused with fluid in a cyclic manner. Moreover, when breathing liquid is evacuated from the lungs, it can be replenished (reoxygenated) in the reservoir and returned to the lungs through the endotracheal tube (or equivalent instrumentation) through subsequent pumping in a later cycle.

The number of cycles for the pumps could be determined by the operator of the device. Optimal compression and expansion of the heart and great vessels is based upon the volume and pressure capacity of the lungs. Cardiac outflow, as a result of the compression and expansion on the heart and great vessels, can then be measured from biocompatible type sensors of blood pressure, capillary blood flow, tissue oxygen, tissue carbon dioxide, tissue pH, tissue lactic acid, blood oxygen, blood carbon dioxide, blood pH, blood lactic acid, EKG, EEG, ultrasound determination of cardiac wall measurement or heart chamber volume, pulse oximetry, pulse carbon dioxide measurement, or the like.

Once the lungs are filled with breathing fluid, substantially the entire fluid volume (the volume infused) could then be evacuated by the pumps (detailed above) operating in reverse. This liquid is then treated in the defoaming units and returned to the reservoirs (where reoxygenation prererably occurs). Liquid from the reservoir is then infused (pumped) into the lungs to repeat the cycle. This cycle can be continued for as long as desired, that is typically until the patient's circulation and breathing are restored.

Alternately, once the lungs have initially been filled with liquid, a smaller volume of liquid (approximately 0.05 to 4.5 liters) is withdrawn and returned to the reservoir to be replenished (reoxygenated) Upon withdrawal of this smaller amount of liquid, the lungs deflate (reduce in volume) slightly, such that the heart and great vessels are subject to less compression by the lungs, and thereby expand. Additional liquid, in amounts approximately equal to that withdrawn from the lungs, would then be pumped into the lungs in pulses or single stroke. This additional amount of liquid could be infused (pumped) into the lungs at a sufficient pressure, to combine with and add to the volume of liquid already in the lungs, whereby the lungs would again expand (increase in volume) to compress the heart and the great vessels.

More preferably, breathing liquid is continuously supplied and withdrawn from the lungs. In the continuous supply of breathing liquid, the lungs are expanded only upon initial filling of the lungs. In other words, normal breathing need not be mimicked in this method. In this method, the efficiency of CPR, for example ACD-CPR, is greatly increased. Further, as discussed below, continuous or sweep flow significantly increase the efficiency of cooling or warming a patient using liquid ventilation.

Figure 5:
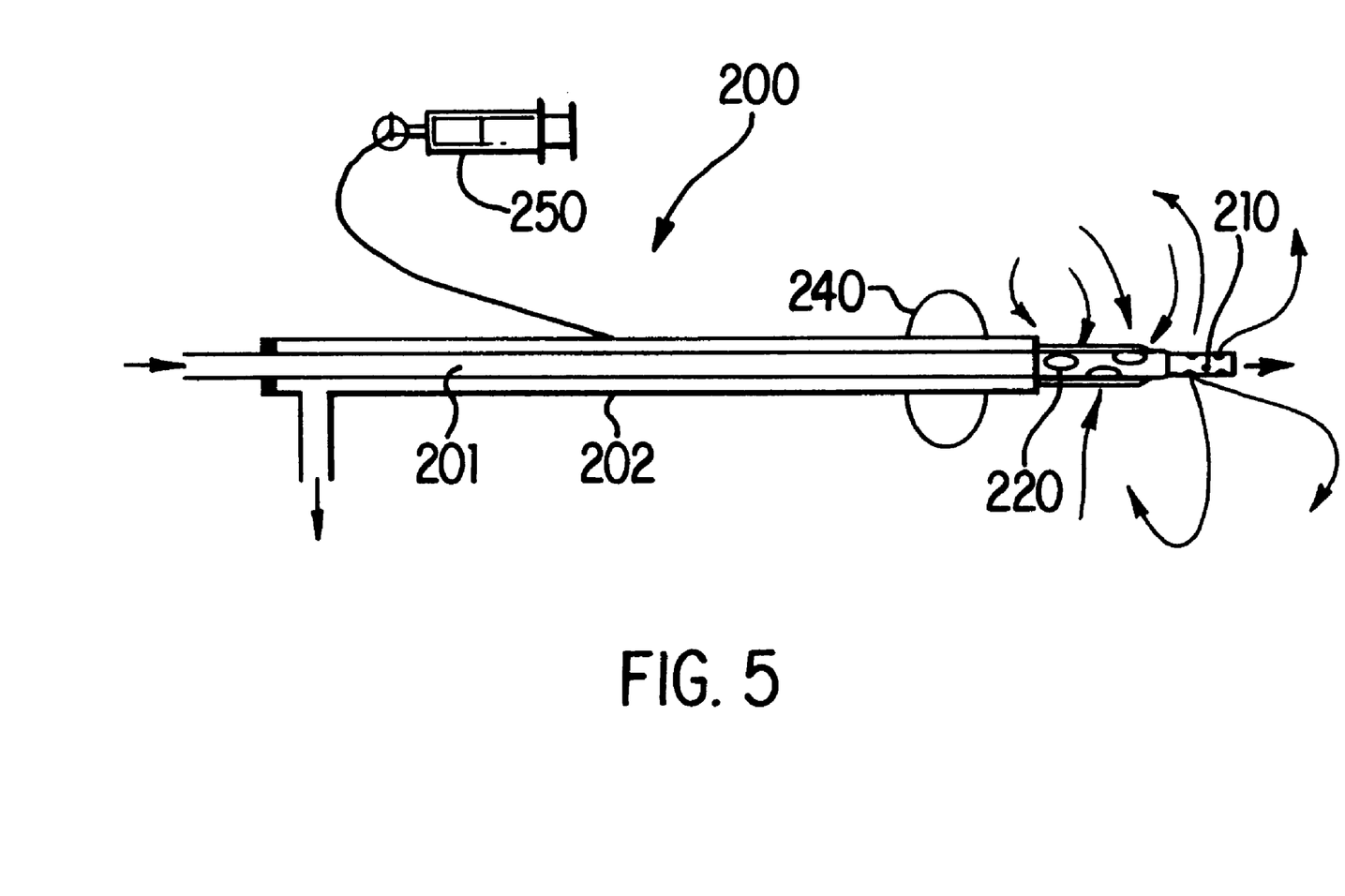
FIG. 5 illustrates a liquid ventilation tracheal tube usable in an embodiment of the invention.

A liquid ventilation tracheal tube for use in continuously supplying and withdrawing breathing liquid to the lungs of a patient is illustrated in FIG. 5. The tube 200 comprises an inner tube 201 and outer tube 202. The smaller, inner tube is connected to the liquid ventilator apparatus and carries the oxygen containing breathing liquid for delivery to the lungs. Thus, the free end of the inner tube is placed in the trachea at a point just above the carina. The end of the inner tube contains openings or fenestrations 210 to deliver the supply of breathing liquid to the lungs. The free end of the inner tube preferably extends beyond the outer tube a distance of about 3 to about 25 mm, preferably about 15 mm, in order to supply a good outflow of breathing liquid.

The outer tube is a return tube for returning spent breathing liquid and other materials to the liquid ventilating apparatus. Thus, the lower portion of the outer tube 202 also contains openings or fenestrations 220 that intake fluid under gravity or pump assisted flow and return the fluid to the apparatus.

The tube 200 also preferably includes a balloon device 240 located just above the openings or fenestrations 220 of the outer tube 202. Once the tube is inserted into the trachea, the balloon device 240 is inflated by any suitable means 250, for example a syringe containing air, to thereby inflate the balloon device to prevent the breathing liquid from escaping in any space between the tube and the trachea.

Figure 6:
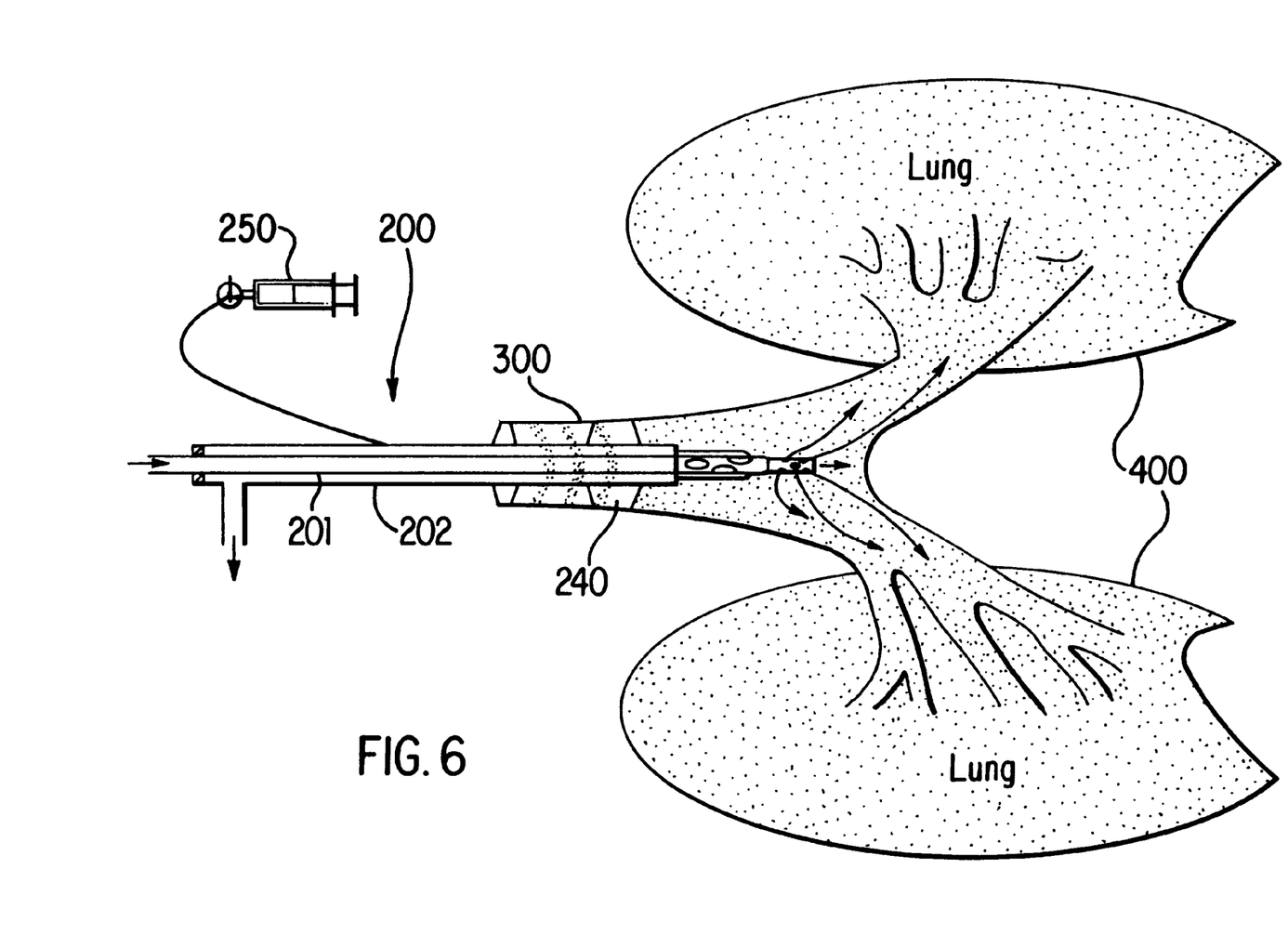
FIG. 6 illustrates the operation of the liquid ventilation tracheal tube of FIG. 5 in the lungs.

FIG. 6 illustrates the placement of tracheal tube 200 in the trachea 300 to deliver the breathing liquid into and withdraw the breathing liquid from lungs 400. As shown in FIG. 6, the balloon device 250 is inflated to prevent the escape of breathing liquid beyond the trachea.

An advantage of this tracheal tube is that the inner tube/outer tube design eliminates the need for the Y-shaped connection described above.

In this method, the ventilating apparatus is preferably capable of continuously supplying breathing liquid into the lungs while simultaneously withdrawing a corresponding amount of breathing liquid. The apparatuses illustrated in FIGS. 1 and 4, as discussed above, may suitably be used for this purpose. A commercially available respirator, the Model 3100A by SensorMedics Critical Care, may also be used once the device is appropriately adapted to be used with liquids in place of gases. The apparatus will also preferably include a pressure control valve to prevent over pressure to the lungs. The pressure control valve turns off the supply of breathing liquid when a high lung pressure threshold is detected.

In the continuous supply of breathing liquid in the lungs in this method, the breathing liquid is preferably supplied at a rate of about four to six liters per minute into the lungs and continuously returned at the same rate to the liquid ventilation apparatus. In conjunction with continuous supply and withdrawal of the breathing liquid, movement and exchange of oxygen containing breathing liquid from the large airways (trachea and bronchi) to the small airways (alveoli) of the lungs where gas exchange takes place is achieved through the use of external CPR, for example Active Compression Decompression CPR (ACD-CPR). During ACD-CPR, which repeatedly supplies a compression and then decompression force, i.e., a positive and negative pressure, on the thoracic cavity through the chest of the patient, the oxygen containing breathing liquid is alternately forced into and withdrawn from the alveoli. During withdrawal of the breathing liquid, spent breathing liquid loaded with carbon dioxide is pulled into fast moving flow in the large airways where it is gathered by the return flow tube and returned to the liquid ventilator for oxygenation and/or cooling or heating.

Continuous liquid ventilation with CPR greatly increases the efficiency of conventional CPR. In replacing the gas in lungs with a breathing liquid, the compliance of the lungs is greatly decreased so that the pressure or pumping force delivered to the heart and large blood vessels of the chest during CPR is greatly increased. Thus, the mean arterial pressure supplied by the CPR is increased. The pressure is thus much more effective in contracting the heart so that the heart valves operate in a more normal fashion and maintain a good supply of oxygen-containing blood to vital organs.

Further, it is not necessary to interrupt the compressions as in conventional CPR for ventilation at every fifth or fifteenth compression because oxygen is being continuously supplied by the breathing liquid. Thus, it is not necessary to interrupt the pumping of blood at any stage of the CPR, which in turn increases cardiac output.

Because there is no air-liquid or air-solid interface when the lungs are filled with the breathing liquid, pleural accumulation of liquid in the event of alveolar rupture will be self-limiting and more easily managed. For example, chest tubes could be used to recover and recycle liquid leaking into the pleural space.

Because the system will be entirely liquid-solid, the hydrostatic pressure inside the alveoli can be controlled, e.g., by using adjustable pressure-limiting valves or other means, and can be matched or increased to slightly above that of the pulmonary artery capillary wedge pressure, thus effectively inhibiting transudation of liquid from the circulatory system to the alveoli.

Because the gas in the lungs is replaced with a liquid, there is no danger of foam formation in the event of transudation of vascular liquid into the alveoli. Such foam greatly decreases gas exchange by forming a mechanical barrier to the movement of air or oxygen and is a major reason for the lethality of fulminating pulmonary edema.

Any vascular liquid which does leak across the alveolar membrane into the liquid breathing medium can be separated out from liquids such as hydrophobic fluorocarbon. If desired, the liquid can be recovered, filtered and returned to the circulatory system, or alternatively, can be discarded and replaced with an appropriate volume of liquid, for example, Plasmalyte, Normosol-R, albumin, dextran solutions (i.e., Gentran), Hespan, etc., through an intravenous line.

Unlike conventional methods, the application of liquid breathing and ACD-CPR does not require connecting a patient in cardiac arrest or in shock to a heart-lung machine or other extracorporeal or intracorporeal vascular devices for oxygenation, blood circulation and/or cooling or rewarming. Since liquid ventilation does not require great skill, essentially anyone with the basic training to place an endotracheal tube or perform a tracheotomy could apply liquid breathing with CPR or liquid breathing with ACD-CPR. In addition, the hazards associated with cardiopulmonary bypass, e.g., air embolism, blood clotting, vascular damage, etc., are absent. Further, there is no time delay for complex surgical procedures to access the circulatory system using this method, as opposed to the use of extracorporeal methods to achieve good restoration of blood flow, gas exchange and cooling or rewarming.

By controlling the temperature of the breathing liquid, the method also permits the rapid cooling and/or rewarming of a patient. Such cooling or warming may be conducted separate from or in conjunction with CPR. Methods for cooling and/or warming the breathing liquid are discussed above, and can also be found in U.S. Pat. No. 5,308,320 (disclosing methods for cooling or warming blood from a patient prior to returning the blood to the patient). The method permits the cooling of a patient's body temperature during cardiac arrest, which in turn decreases the patient's metabolic demands and protects the patient from brain damage. Once the patient has been resuscitated and hypothermically treated, the patient's body temperature may be returned to normal body temperature from the lowered temperature where the heart had stopped.

The continuous supply and withdrawal of the breathing liquid is far more effective in heating and cooling a patient compared to the above-discussed pulse liquid only ventilation resuscitation method of supplying and withdrawing the breathing liquid in pulses. While the pulse method successfully meets the gas exchange demands, the heat exchange remains low due to the low rate of pulse ventilations, approximately five to seven per minute, and the total flow rate of liquid in and out the lungs being about 2,000 ml/min. By contrast, in continuous liquid ventilation, about four to about six liters per minute of breathing liquid are exchanged in the lungs, which in turn greatly increases the ability to chill and/or warm the patient.

For example, if the breathing liquid is sufficiently cooled and liquid ventilation is used in conjunction with external cooling methods such as ice water immersion or colonic and peritoneal lavages with cold solutions, it is possible to achieve a cooling rate of about 1.5 to about 2.0° C./min. in an average human adult of 65 kilograms. For this, the liquid breathing material is preferably cooled to a temperature of from −10° C. to 30° C., and more preferably between −3° C. and 25° C. The patient can be substantially cooled, for example down to 0° C., using chilled liquid breathing materials.

The method thus has the ability to achieve a rapid induction of hypothermia, which in turn causes reduced cerebral and whole-body metabolic demands and thus provides substantial cerebro-protection against the "delayed neuronal death phenomenon" that would otherwise follow an ischemic insult.

Since all of the cardiac output flows through the lungs with their large surface area available for heat exchange using a liquid medium, it will be possible to rapidly cool and/or rewarm a mammalian body by controlling the temperature of the breathing liquid. The importance of the prompt induction of hypothermia in providing immediate and delayed cerebral protection following cardiac arrest, shock, and regional and global cerebral ischemia is well known in the art.

It has been shown in this laboratory that in states of shock, cardiac arrest, or diminished cardiac output, the brain is selectively shunted blood flow at the expense of the rest of the body. Thus, the brain is preferentially cooled by the application of chilled gas or chilled liquid to the pulmonary airspace.

At temperatures below normal body temperature, deterioration under hypoxic or toxic conditions is slowed. Prior applications of pulsed liquid ventilation for cooling were restricted to about at most a 20% reduction in body temperature. See, for example, U.S. Pat. No. 5,395,314. With continuous or sweep flow cooling, however, cooling can be profound enough to permit transitioning to total body washout for stabilization near 0° C. for up to 8 hours. Such temperature control may alone allow up to an additional eight hours of organ viability, without neurologic damage.

As stated previously, delivery of the chilled liquid breathing solution for augmenting CPR may be continuous or pulsatile, cyclic or non-cyclic, depending upon the type of the pumps, logic control units and devices (disclosed above) in use for the specific method.

The liquid breathing material comprises about 0 to 100 percent by volume of a base oxygen carrying material, preferably 10 to 99, more preferably 50 to 95, percent by volume of the base oxygen carrying material. Perfluorocarbons, for example Perflubron™ and other perfluorochemicals, hemoglobin based blood substitutes, or non-hemoglobin based blood substitutes are the preferred oxygen carrying agents, as they have an extremely high oxygen capacity. Also suitable is CryoVent, a trademark of BioPreservation, Inc. (Rancho Cucamonga, Calif.). When delivered to the lungs, in the oxygenation step, these oxygen carrying materials may be supersaturated with oxygen, either having been oxygenated in the fluid reservoir or preoxygenated.

The oxygen carrying materials that typically comprise the majority of the breathing liquid should have a high oxygen solubility, including at low temperatures, for example on the order of 10 to 70 ml/100 ml at 0° C. or 25° C. The agent should also have a high solubility of carbon dioxide at low temperatures, on the order of 10 ml to 300 ml/100 ml of the agent so as to permit good gas exchange at low temperatures. The agents are preferably more dense than water so that when chilled, they will remove heat in an efficient manner, on the order of 1,000 times more efficient then air, oxygen and other gases.

The breathing liquid may include small amounts of nitric oxide, a blood vessel dilator. Nitric oxide acts to increase the blood flow so that in combination with the breathing liquid, blood flow in lung tissues which the breathing liquid reaches is selectively improved. Perfluorocarbons such as FC11 can carry nitric oxide. In cases in which the liquid ventilation solution is aqueous or has a significant aqueous component, therapeutic drugs, vitamins, nutrients, chelators, hormones, and other agents well known in the art may be supported in the ventilation medium.

The method of the invention may also be used to provide circulation in non-cardiac arrest situations. For example, it may be used to enhance circulation for patients with congestive heart failure. Also, it may be used to create/improve circulation in patients suffering from cardiac tamponade, electro-mechanical dissociation, lethal cardiac arrhythmia, or ineffective cardiac arrhythmia.

This method can also facilitate delivery of drugs that might be contained in the breathing liquid by, for example, dissolving the drugs in the liquid breathing material or forming an emulsion with the drugs in the breathing liquid. Drug delivery is facilitated as the solution infused into the lungs is absorbed into the lung tissues and other associated tissues by capillary absorption or diffusion across the membranes of the alveoli. These absorbed materials could then reach the bloodstream when the lungs oxygenate the blood during circulation.

The method of the invention may also be used to rapidly and effectively restore gas exchange and limit lung injury in a patient's lung that is filled with water. As discussed above, the breathing liquid is denser than water and thus is able to rapidly reinflate collapsed or water-logged portions of the lung, forcing water out of the lungs.

In an alternative method, the continuous liquid flow could be replaced by continuous gas flow using 20%–100% $O_2$. In other words, a standard endotracheal tube could be modified to have an inner tube with a fenestration which is placed at the level of the carina and through which is passed 10–40 LPM of 20%–100% oxygen as necessary to eliminate the "dead-space" which is a major limiting step on the efficacy of ventilation using ACD-CPR, without pausing to interpose a ventilation after each fifth chest compression/ decompression. Such a device would be simple to manufacture, easy to supply and would greatly increase the efficacy of ACD-CPR. In fact, in preliminary experiments it doubles $SVO_2$ in dogs undergoing ACD-CPR in whom no pause for ventilation is used at a sweep gas flow rate of 15 LPM.

EXAMPLE

Dogs having an average weight of 25 kg were anesthetized. Baseline MAP and cardiac output (CO) before cardiac arrest was induced were 90 mm Hg and 1.45 liters per minute (LPM), respectively. CPR with and without liquid ventilation was applied and the results were compared. With liquid ventilation, MAPs of up to 140 mm Hg were achieved. Without liquid ventilation, the average MAP value was only 35 mm Hg. In addition, with liquid ventilation, the CO values obtained were in the range of 0.9 to 1.3 LPM. Without liquid ventilation, the CO values obtained were in the range of 0.30 to 0.45 LPM. Thus, the use of liquid ventilation to eliminate pulmonary compliance and increase the efficacy of CPR significantly raises cardiac output and MAP in dogs undergoing CPR.

While this invention has been described in conjunction with specific embodiments thereof, it is evident that many alternatives, modifications and variations will be apparent to those skilled in the art. Accordingly, the preferred embodiments of the invention as set forth herein are intended to be illustrative, not limiting. Various changes may be made without departing from the spirit and scope of the invention as defined above.

What is claimed is:

1. A cardiopulmonary resuscitation method, comprising providing a breathing liquid to lungs of a mammal and cyclically applying an external thoracic cavity pressure inducing force to a thoracic cavity of the mammal only when the lungs of the mammal are substantially filled with the breathing liquid, wherein the breathing liquid delivers oxygen to the lungs and collects carbon dioxide from the lungs.

2. The method of claim 1, wherein the method further comprises placing a tracheal tube in a trachea of the mammal for delivery and withdrawal of the breathing liquid from the lungs.

3. The method of claim 1, wherein the breathing liquid is provided continuously to the lungs.

4. The method of claim 3, wherein the breathing liquid is provided at a volume of about 4 to about 6 liters per minute.

5. The method of claim 1, wherein the external thoracic cavity pressure varies between a positive pressure and a negative pressure.

6. The method of claim 1, wherein the breathing liquid is provided cyclically to the lungs.

7. The method of claim 1, wherein the breathing liquid comprises perfluorocarbon, hemoglobin based blood substitutes or non-hemoglobin based blood substitutes.

8. The method of claim 7, wherein the breathing liquid comprises perfluorocarbon.

9. The method of claim 1, wherein the breathing liquid is provided to the lungs at below a normal body temperature of the mammal.

10. The method of claim 9, wherein the breathing liquid is provided to the lungs at 30° C. or less.

11. The method of claim 1, wherein the method further comprises evacuating the lungs of air and other materials prior to providing the breathing liquid.

12. The method of claim 1, wherein the breathing liquid is provided from an apparatus comprising:

a reservoir for holding breathing liquid;

a source of oxygen for oxygenating the breathing liquid and in communication with the reservoir;

a heat exchanger for cooling or warming the breathing liquid;

one or more tubes in communication with the reservoir for transporting the breathing liquid to and from the apparatus; and one or more valves associated with the one or more tubes for controlling the flow of breathing liquid to and from the apparatus.

* * * * *